United States Patent [19]

Bollinger et al.

[11] 4,210,439
[45] Jul. 1, 1980

[54] N-SUBSTITUTED OXOBENZOTHIAZOLINES AND THEIR USE AS PLANT GROWTH REGULATORS

[75] Inventors: Frederic G. Bollinger, Creve Coeur; John J. D'Amico, Olivette, both of Mo.

[73] Assignee: Monsanto Company, St. Louis, Mo.

[21] Appl. No.: 863,498

[22] Filed: Dec. 22, 1977

[51] Int. Cl.$^2$ .................. A01N 9/12; C07D 277/68
[52] U.S. Cl. ............................ 71/90; 548/170; 71/74; 71/76; 71/77
[58] Field of Search .................. 260/304 B; 71/90

[56] References Cited

U.S. PATENT DOCUMENTS

| 3,069,429 | 12/1962 | Godron et al. ............ 260/304 |
| 3,544,302 | 12/1970 | Hamm ........................ 71/90 |
| 3,661,921 | 5/1972 | Umio .......................... 260/304 B |
| 4,032,320 | 6/1977 | Lush ........................... 71/90 |
| 4,049,419 | 9/1977 | D'Amico ..................... 260/304 B |
| 4,093,447 | 6/1978 | Metzger et al. ............ 71/111 |

FOREIGN PATENT DOCUMENTS

| 46-21378 | 6/1971 | Japan ........................... 71/90 |
| 862226 | 3/1961 | United Kingdom .......... 260/304 B |

OTHER PUBLICATIONS

Zinner et al., Chem. Abst., 83, 114267M (1975) Abst. of J. Prakt. Chem, B117, pp. 379–386 (1975).

*Primary Examiner*—Donald G. Daus
*Assistant Examiner*—W. B. Springer
*Attorney, Agent, or Firm*—Patricia A. Coburn; Donald W. Peterson

[57] ABSTRACT

This invention relates to novel N-substituted oxobenzothiazolines and to their use in a method of regulating leguminous plant growth as well as to plant growth regulant compositions.

24 Claims, No Drawings

N-SUBSTITUTED OXOBENZOTHIAZOLINES AND THEIR USE AS PLANT GROWTH REGULATORS

BACKGROUND OF THE INVENTION

This invention relates to new N-substituted oxobenzothiazolines and to their use in a method of regulating leguminous plant growth as well as to plant growth regulant compositions.

In recent years it has been recognized that there exists a great need for expanding the world's food production as well as a need for more efficient use of available energy. Recognition of these needs has stimulated interest in controlling plant growth processes to obtain more efficient productivity through the use of plant growth regulants. Unfortunately, the understanding of plant physiological processes is incomplete and much research remains to be done before the potential uses of plant growth regulants are ascertained. It can be readily appreciated, therefore, that new compounds which are useful in regulating plant growth, especially growth of crop plants fill important agricultural and economic needs and provide further knowledge for our understanding of plant physiological processes.

It is presently known that certain benzothiazyl compounds possess herbicidal activity. U.S. Pat. No. 3,069,429 discloses the use of derivatives of 4-halogeno-2-oxobenzothiazolin-3-ylacetic acid to kill weeds. U.S. Pat. No. 3,651,074 discloses the use of certain 2-oxo-3-benzothiazolines as a herbicide. Neither of these patents, however, disclose the use of the specific benzothiazolines used in accordance with the present invention to regulate the growth of plants.

It is further known that certain benzothiazyl compounds possess plant growth regulating activity. U.S. Pat. No. 2,468,075 discloses the use of such compounds as abcission agents. Japanese Patent No. 71/21378 discloses that such compounds possess plant growth regulating activity, but does not disclose any specific uses. Japanese Pat. No. 73/10182 discloses the use of benzothiazyl compounds as grafting agents for tree root growth. U.S. Pat. No. 3,993,468 and U.S. Pat. No. 4,049,419 disclose the use of certain benzothiazolines as plant growth regulants. Neither of these patents, however, disclose the use of the specific benzothiazolines used in accordance with the present invention.

DESCRIPTION OF THE INVENTION

The invention relates to a new class of chemical compounds and their use as plant growth regulants. More specifically, the invention relates to novel N-substituted oxobenzothiazoline compounds useful in regulating the growth of leguminous plants.

N-substituted oxobenzothiazolines useful in accordance with this invention are represented by the formula

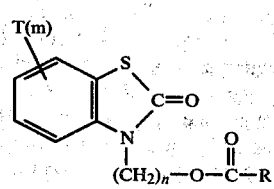

wherein R is lower alkyl, T is chloro, $NO_2$, lower alkyl or lower alkoxy, m is 0 or 1 and n is an integer from 1 to 2.

The N-substituted oxobenzothiazoline compounds useful as plant growth regulants in the present invention are generally described by the formula given above and particularly and specifically include, although not limited to, the following compounds: Acetic Acid, [2(2-oxo-3-benzothiazolinyl)ethyl]ester; Propionic Acid, [2-(2-oxo-3-benzothiazolinyl)ethyl]ester; Acetic Acid, [alpha-(2-oxo-3-benzothiazolinyl)methyl]ester; Acetic Acid, [3-(2-oxo-3-benzothiazolinyl)propyl]ester; Valeric Acid, ([2-(2-oxo-3-benzothiazolinyl)ethyl]ester; Isobutyric Acid, [2-(2-oxo-3-benzothiazolinyl)ethyl]ester; Isovaleric Acid, [2-(2-oxo-3-benzothiazolinyl)ethyl]ester; Acetic Acid, [2-(5-chloro-2-oxo-3-benzothiazolinyl)ethyl]ester; Acetic Acid, [2-(6-ethoxy-2-oxo-3-benzothiazolinyl)ethyl]ester; Acetic Acid, [2-(6-nitro-2-oxo-3-benzothiazolinyl)ethyl]ester.

In the description of the novel N-substituted oxobenzothiazolines useful as plant growth regulants of this invention, the following embodiments are intended for the various groups. The term lower alkyl includes those members including straight chain and branched chain, having from 1 to 5 carbon atoms, inclusive, for example, methyl, ethyl, n-propyl, isopropyl, n-butyl, sec-butyl, tert-butyl, n-pentyl, isopentyl, and the like. The term lower alkoxy preferably includes those members, including straight chain and branched chain, having from 1 to 5 carbon atoms, inclusive, for example, methoxy, ethoxy, n-propoxy, isopropoxy, n-butoxy, sec-butoxy, tert-butoxy, n-butoxy, isopentoxy and the like.

The term "plant regulant," as employed in this application, connotes a material which serves to modify the normal sequential development of a desirable crop plant to agricultural maturity. Such modification may result from the effect of the material on the physiological processes of the plant or from the effect of said material on the morphology of the plant. It should additionally be recognized that modifications may also result from a combination or sequence of both physiological and morphological factors.

Modifying effects of a plant regulant are probably most readily observed as changes in the size, shape, color or texture of the treated plant or any of its parts. Similarly, changes in the quantity of the plant fruit or flowers are also quite apparent from visual inspection. The above changes may be characterized as an acceleration or retardation of plant growth, stature reduction, leaf or canopy alteration, increased branching, tillering, terminal inhibition, increased flowering or fruit set, increased root growth, axillary bud development or inhibition, delayed budding, defoliation, desiccation, delayed senescence, prolongated dormancy, increased cold hardiness, delayed or accelerated ripening, and the like.

Modification in the normal sequential development of a treated plant or agricultural maturity may also be manifested by reduced transpiration or increased carbohydrate deposition or protein content.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatures and are more resistant to pest infestations and to lodging. Further, a reduction in the maturation rate on portions of a crop permits an extended harvest period at peak yield and more efficient use of subsequent crop processing equipment.

It is to be understood that the regulation of desirable crop plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

In accordance with this invention it has been found that desirable modification of plants is achieved by applying the above-described plant regulants to the "plant locus." The term "plant locus" is understood herein to include the plant growing medium, such as the soil, as well as the seeds, emerging seedlings, roots, stems, leaves, flowers, fruits or other plant parts.

The term "active ingredient" is used herein to describe the active N-substituted oxobenzothiazoline compounds of the foregoing formula. Generally, the novel N-substituted oxobenzothiazoline compounds are prepared by the following reactions:

Method I.

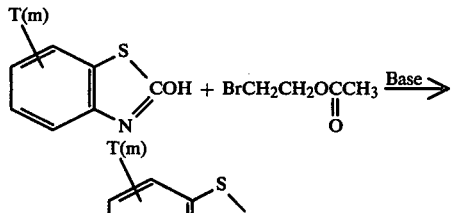

Method II.

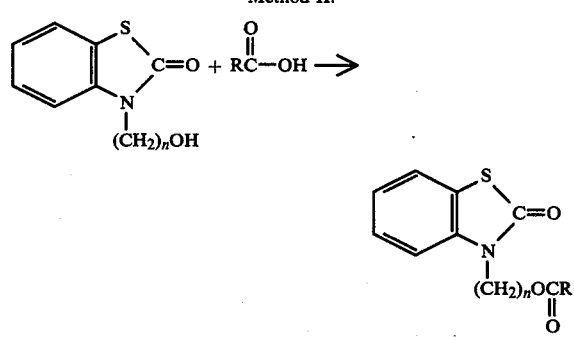

The hydroxyl alkyl benzothiazolinones used as the starting material in Method II may be prepared according to the following examples.

EXAMPLE 1

To a stirred slurry containing 30.2 g (0.2 mol) of 2-hydroxybenzothiazole and 40 ml of methyl alcohol, 32 ml of 37% aqueous formaldehyde was added in one portion. The stirred mixture was heated at 78°–80° C. (reflux) for 30 minutes. At 80° C., 60 ml of hot water was added to the stirred solution. After cooling to 0° C., the product was collected by filtration, washed with 100 ml of heptane and air-dried at 25°–30° C. The product, 3-(hydroxymethyl)-2-benzothiazolinone, mp. 101°–3° C., was obtained in 94% yield. After recrystallization from isopropyl alcohol the melting point remained unchanged.

Anal. Calc'd for $C_8H_7NO_2S$: N, 7.73; S, 17.70; Found: N, 7.95; S, 17.89.

EXAMPLE 2

To a stirred solution containing 151.2 g (1.0 mol) of 2-hydroxybenzothiazole, 66 g (1.0 mol) of 85% potassium hydroxide and 300 ml of water, 88.6 g (1.1 mol) of 2-chloroethanol was added in one portion. The stirred reaction mixture was heated at 90°–100° C. for 5 hours and at 25°–30° C. for 18 hours. After cooling to 10° C., the reaction mixture was stirred at 0°–10° C. for 30 minutes. The product, 3-(2-hydroxyethyl)-2-benzothiazolinone, was collected by filtration and air-dried at 25°–30° C. The product, mp. 90°–92° C. was obtained in 98% yield. After recrystallization from toluene, it melted at 94°–95° C.

Anal. Calc'd for $C_9H_9NO_2S$: N, 7.17; S, 16.42; Found: N, 7.11; S, 16.12.

The compounds of this invention represented by the following formula

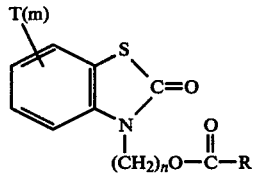

can be prepared according to Methods I and II, described previously. The following examples are given for the purpose of illustrating methods of preparing the novel N-substituted oxobenzothiazoline compounds useful as plant growth regulants in the present invention.

EXAMPLE 3

To a stirred solution containing 0.1 mol of the appropriate 2-hydroxybenzothiazole, 6.6 g (0.1 mol) of 85% potassium hydroxide, 150 ml of dimethylformamide and 10 ml of water, 18.4 g (0.11 mol) of 2-bromoethyl acetate was added in one portion. The reaction mixture was stirred at 90°–100° C. for 2 days and at 25°–30° C. for 1 day. For compounds 2 and 4 (listed in Table I), 800 g of ice water was added and stirring continued at 0°–10° C. for one hour. The solid was collected by filtration, washed with water until neutral to litmus and air-dried at 25°–30° C. For compounds 1 and 3 (listed in Table I), 600 ml of water and 500 ml of ethyl ether were added and stirring continued at 25°–30° C. for 15 minutes. The separated ether layer was washed with water until neutral to litmus and dried over sodium sulfate. The ether was removed in vacuo at maximum temperature of 80°–90° C. at 1–2 mm.

Table I lists the data obtained when the N-substituted oxobenzothiazoline compounds of the present invention were prepared in accordance with Example 3.

TABLE I

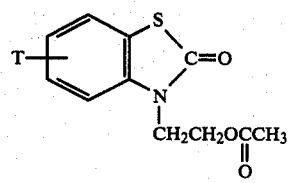

| Compound No. | T | M.P. °C. | % Yield | % C Calcd. | % C Found | % H Calcd. | % H Found | % N Calcd. | % N Found | % S Calcd. | % S Found |
|---|---|---|---|---|---|---|---|---|---|---|---|
| 1 | H | viscous liquid $n_D^{25} = 1.5900$ | 84 | — | — | — | — | 5.90 | 6.05 | 13.51 | 13.59 |
| 2 | 5-Cl | 63–65[a] | 79 | 48.62 | 48.77 | 3.71 | 3.48 | 5.15 | 5.39 | 11.80 | 11.55 |
| 3 | 6-OC$_2$H$_5$ | viscous liquid | 87 | — | — | — | — | 5.28 | 5.29 | 12.08 | 12.11 |
| 4 | 6-NO$_2$ | 130–131[b] | 78 | — | — | — | — | 9.92 | 10.34 | 11.36 | 11.86 |

[a]Recrystallization from heptane/isopropyl alcohol (4:1).
[b]Recrystallization from methyl alcohol/ethyl acetate (4:1).

EXAMPLE 4

A stirred mixture containing 0.2 mol of 3-(hydroxymethyl)-2-benzothiazolinone, 0.25 mol of acetic acid, 4 g of para-toluenesulfonic acid and 200 ml of toluene was heated at reflux for 6 hours or until 3.6 ml of water was collected via a Dean Stark Condenser. After stirring at 25°–30° C. for 18 hours, 20 g (0.25 mol) of 50% sodium hydroxide and 300 ml of water were added. This was followed by the addition of 500 ml of ethyl ether and stirring was continued for 15 minutes. The separated top organic layer was washed with water until neutral to litmus and dried over sodium sulfate. The ether and toluene were removed in vacuo at a maximum temperature of 80°–90° C. at 1–2 mm. Compound No. 5 in Table II was obtained.

Compounds 6–9 of Table II were prepared in a similar manner. The starting material for these compounds was 3-(hydroxyethyl)-2-benzothiazolinone and the reacting acid was as follows:

| Compound No. | Acid |
|---|---|
| 6 | propionic |
| 7 | isobutyric |
| 8 | valeric |
| 9 | isovaleric |

The data obtained when the N-subsituted oxobenthiazoline compounds of the present invention were prepared in accordance with Example 4 is listed in Table II.

TABLE II

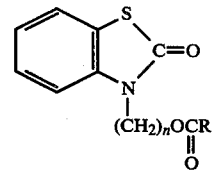

| Compound No. | n | R | State | % Yield | % N Calcd. | % N Found | % S Calcd. | % S Found |
|---|---|---|---|---|---|---|---|---|
| 5 | 1 | —CH$_3$ | viscous liquid | 25 | 6.27 | 6.39 | 14.36 | 14.45 |
| 6 | 2 | —CH$_2$CH$_3$ | viscous liquid $n_D^{25} = 1.5744$ | 78 | 5.57 | 5.70 | 12.76 | 12.94 |
| 7 | 2 | —CH(CH$_3$)$_2$ | viscous liquid $n_D^{25} = 1.5642$ | 91 | 5.27 | 5.33 | 12.08 | 12.19 |
| 8 | 2 | —CH$_2$CH$_2$CH$_2$CH$_3$ | viscous liquid $n_D^{25} = 1.5620$ | 70 | 5.01 | 5.16 | 11.47 | 11.63 |
| 9 | 2 | —CH$_2$CH(CH$_3$)$_2$ | viscous liquid $n_D^{25} = 1.5555$ | 84 | 5.01 | 4.90 | 11.47 | 11.56 |

In practicing the plant growth regulating methods of this invention, the active ingredients can be used alone or in combination with a material referred to in the art as an adjuvant in liquid or solid form. The plant growth regulating compositions of this invention are prepared by admixing the active ingredients with an adjuvant including diluents, extenders, carriers and conditioning agent to provide compositions in the form of finely-divided particulate solids, granules, pellets, wettable powders, dusts, solutions and aqueous dispersions or emulsions. Thus, the active ingredient can be used with an adjuvant such as a finely divided particulate solid, a solvent liquid of organic origin, water, a wetting agent, dispersing agent, or emulsifying agent or any suitable combination of these.

Illustrative finely divided solid carriers and extenders which are useful in the plant growth regulating compositions of this invention, include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents include, for example, Stoddard solvent, acetone, alcohols, glycols, ethyl acetate, benzene and the like. The plant growth regulating compositions of this invention, particularly liquids and wettable powders, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein. Such surface-active agents are well known and are illustrated in detail in U.S. Pat. No. 2,547,724, Columns 3 and 4.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters, petroleum sulfonate, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose polyvinyl alcohol, sodium lignin sulfonates, polymeric alkyl naphthalene sulfonates, sodium naphthalene sulfonate, polymethylene bisnaphthalenesulfonate and sodium N-methyl-N-(long chain acid) laurates.

Water-dispersible powder compositions can be made containing one or more active ingredients, an inert solid extender and one or more wetting and dispersing agents. The water-dispersible powder of this invention usually contain from about 5 to about 95 parts by weight of active ingredient, from about 0.25 to 25 parts by weight of wetting agent, from about 0.25 to 25 parts by weight of dispersant and from 4.5 to about 94.5 parts by weight of inert solid extender, all parts being by weight of the total compositions. If desired, from about 0.1 to 2.0 parts by weight of the solid inert extender can be replaced by a corrosion inhibitor or anti-foaming agent.

Aqueous suspensions can be prepared by mixing together and grinding an aqueous slurry of water-insoluble active ingredient in the presence of dispersing agents to obtain a concentrated slurry of finely-divided particles. The resulting concentrated aqueous suspension is characterized by its extremely small particle size, so that when diluted and sprayed uniform coverage is obtained.

Emulsifiable oils are usually solutions of active ingredient in water-immiscible or partially water-immiscible solvents together with surface-active agent. Suitable solvents for the active ingredient of this invention include hydrocarbons and water-immiscible ethers, esters or ketones. The emulsifiable oil compositions generally contain from about 5 to 95 parts active ingredient, about 1 to 50 parts surface-active agent and about 4 to 94 parts solvent, all parts being by weight based on the total weight of emulsifiable oil.

The application of liquid and particulate solid compositions of the active ingredient can be carried out by conventional techniques utilizing, for example, spreaders, power dusters, boom and hand sprayers and spray dusters. The compositions can also be applied from airplanes as a dust or spray. The application of the plant growth regulating compositions to the plant growth medium is generally carried out by incorporating the compositions in the soil or other media in the area where modification of the plants is desired.

In selecting the appropriate non-toxic rate of application of the active ingredient it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts from about 0.05 to about 10 or more pounds per acre. Foliar applications of from 0.1 to 5 pounds of the active ingredient per acre are preferred. In applications to the soil habitat of germinant seeds, emerging seedlings, and established vegetation for the regulation of plant growth, the active ingredients are applied in amounts of from about 0.01 to about 20 pounds per acre or more. Preferably, the active ingredients are applied to the soil at a rate of from 0.01 to 10 pounds per acre. Foliar application to plants beginning to blossom is particularly advantageous and is preferred.

In accordance with the present invention, the novel oxobenzothiazolinyl esters are found to be effective growth regulators for leguminous plants, as represented by soybean (Glycine max).

In accordance with the practice of the invention, several plant growth regulating compositions were formulated utilizing several of the novel oxobenzothiazolinyl esters as the active ingredient. The compositions were formulated so that they could be applied at a rate the equivalent of 200 gallons per acre (306 liters per hectare). Table III illustrates the formulation of the composition for several application rates of active ingredient. The formulation of the composition for other rates of application is well within the skill of the art. In each formulation, the stock solution utilized is 1% of the active ingredient dissolved in acetone.

TABLE III

| RATE Lbs/Acre | (kilos hectare) | ml of 1% Stock Solution | ml Acetone | ml of 0.39% TWEEN 20 In Water As Surfactant |
|---|---|---|---|---|
| 6.0 | (6.72) | 2.0 | — | 3.6 |
| 5.0 | (5.60) | 2.0 | 1.0 | 3.7 |
| 3.0 | (3.36) | 1.0 | 1.0 | 3.6 |
| 2.5 | (2.80) | 1.0 | 2.0 | 3.7 |
| 1.2 | (1.34) | 0.4 | 1.6 | 3.6 |
| 1.0 | (1.12) | 0.4 | 2.6 | 3.7 |
| 0.5 | (0.560) | 0.2 | 2.8 | 3.7 |
| 0.3 | (0.336) | 0.1 | 1.9 | 3.6 |

Utilizing compositions formulated in accordance with TABLE I, several oxobenzothiazolinyl esters exhibited unexpected plant growth regulating properties as illustrated by the test set forth in Example 5.

EXAMPLE 5

A number of soybean plants, variety Corsoy, are grown from seeds in aluminum pans in a greenhouse for a period of approximately one week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. An aqueous composition of the active ingredient is then applied to the pan of growing plants by overhead spray at a rate equivalent to 6 pounds of chemical per acre. The treated pans, along with the control pans, are maintained in a greenhouse and watered from below on a sand bench and fertilized with a uniform portion of a water-soluble balanced fertilizer.

Two weeks after application of the chemical the average height of the soybean plants in the treated pan is again measured as above and the difference in the average height before and two weeks after application represent the increase in the development of the treated plants. This development in growth of the treated plants is compared to the average increase in growth of the plants in the control pans during the same period of time. A variation of 25% or more in the development of at least two-thirds of the treated plants were compared to the development of the control plants demonstrates that the chemical is an effective plant regulant. Thus, a chemical is considered active when the treated plants manifest a decrease in growth of at least 25% less than that of the control plants, i.e., stature reduction or an increase in growth in excess of 25% of that of the control plants, i.e., growth stimulation.

Table IV summarizes the results for observations made in accordance with Example 5 when the novel N-substituted oxobenzothiazoline compounds of the present invention are utilized as the active ingredient at several application rates.

EXAMPLE 6

Individual soybean plants, variety Corsoy, are grown from seed in 6-inch pots containing a good grade of top soil. Two pots of 4 week old plants (3–4 trifoliate stage) and two pots of 6-week old plants (5–6 trifoliate stage) are used for each application of the chemical. An overhead spray of an aqueous composition of the chemical is applied to the pots at an equivalent rate as indicated below. Two to four sets of plants which received no chemical application are included and serve as controls. All of the pots are maintained under good growing conditions and are watered and fertilized with a uniform amount of a water-soluble balanced fertilizer. Two weeks after the application of the chemical, the growth responses of the treated plants are compared with that of the control plants. The total height of the plant is measured to the tip of the terminal bud. A variation of 15 percent in the average total height of the treated plants, when compared to the average total height of the control plants, demonstrates that the chemical is an effective plant growth regulator. These observations are repeated at four weeks after chemical application as a further evaluation of plant regulatory activity. The observations made on 4-week and 6-week-old plants, at

TABLE IV

| Active Ingredient (R) | (n) | (T) | RATE Lbs Acre | Kilos Hectare | Response |
|---|---|---|---|---|---|
| —CH$_3$ | 2 | H | 6.0 | 6.72 | Leaf distortion inhibition of apical development. |
| | | | *6.0 | 6.72 | Stature reduction, leaf inhibition, inhibition of apical development, leaf distortion. |
| | | | *3.0 | 3.36 | Stature reduction, leaf inhibition, inhibition of apical development, leaf distortion. |
| | | | *3.0 | 3.36 | Leaf distortion, stem distortion. |
| | | | *2.0 | 2.24 | No response observed. |
| | | | *1.2 | 1.34 | Stature reduction, leaf distortion, inhibition of apical development. |
| | | | *1.2 | 1.34 | No response observed. |
| | | | *0.6 | 0.67 | No response observed. |
| —CH$_2$CH$_3$ | 2 | H | 6.0 | 6.72 | Stature reduction, leaf distortion, inhibition of apical development. |
| | | | 6.0 | 6.72 | Stature reduction, leaf distortion, stem distortion, slight leaf burn. |
| | | | 3.0 | 3.36 | Leaf distortion, stem distortion. |
| | | | 1.20 | 1.34 | Leaf alteration, leaf distortion, stem distortion. |
| —CH(CH$_3$)$_2$ | 2 | H | 6.0 | 6.72 | Stature reduction, leaf distortion, inhibition of apical development, stem distortion. |
| | | | 6.0 | 6.72 | Leaf distortion, inhibition of apical development, slight leaf burn. |
| | | | 3.0 | 3.36 | Leaf distortion, inhibition of apical development, slight leaf burn. |
| | | | 1.2 | 1.34 | Leaf distortion, inhibition of apical development. |
| —CH$_2$—CH$_2$CH$_2$CH$_3$ | 2 | H | 6.0 | 6.72 | Leaf distortion. |
| | | | 6.0 | 6.72 | Axillary bud development, leaf distortion, thick leaf texture, slight leaf burn. |
| | | | 3.0 | 3.36 | Leaf distortion, axillary bud development. |
| | | | 1.2 | 1.34 | Leaf distortion. |
| —CH$_2$CH$_2$(CH$_3$)$_2$ | 2 | H | 6.0 | 6.72 | Leaf distortion, thick leaf texture, epinasty, slight leaf burn. |
| | | | 3.0 | 3.36 | Inhibition of apical development, thick leaf texture, leaf distortion. |
| | | | 3.0 | 3.36 | Inhibition of apical development, thick leaf texture, leaf distortion. |
| | | | 1.2 | 1.34 | Inhibition of apical development, thick leaf texture, leaf distortion. |
| | | | 0.6 | 0.67 | Inhibition of apical development, leaf distortion. |
| —CH$_3$ | 1 | H | 6.0 | 6.72 | Slight leaf burn. |

*Test chemical applied at first leaf stage; one plant/pot sprayed; otherwise procedure used was that described in Example 5.

Further advantages of this invention are shown in Example 6.

2 and 4 weeks form a composite evaluation.

Observations made utilizing the test procedure of Example 6 are summarized in Table V.

TABLE V

| Active Ingredient (R) | (n) | (T) | RATE Lbs Acre | RATE Kilos Hectare | Response |
|---|---|---|---|---|---|
| —CH$_3$ | 2 | H | 5.0 | 5.60 | Stem distortion, selective apical kill, delayed pod set, slight leaf burn, inhibited pod set. |
| | | | 2.5 | 2.80 | Stature reduction, slight leaf burn. |
| | | | 1.0 | 1.12 | No response observed. |
| | | | 0.5 | 0.56 | Early pod set. |
| —CH$_2$CH$_3$ | 2 | H | 2.5 | 2.80 | Delayed pod set, inhibited pod set. |
| | | | 1.0 | 1.12 | Delayed pod set. |
| | | | .5 | 0.56 | Delayed pod set, inhibited pod set. |
| —CH(CH$_3$)$_2$ | 2 | H | 5.0 | 5.60 | Early pod set, enhanced pod set, axillary bud inhibition, leaf distortion, moderate leaf burn. |
| | | | 5.0 | 5.60 | Stature reduction, early pod set, enhanced pod set, leaf inhibition, leaf distortion, slight leaf burn. |
| | | | 2.5 | 2.80 | Epinasty, slight leaf burn. |
| | | | 2.5 | 2.80 | Early pod set, enhanced pod set, leaf distortion. |
| | | | 1.0 | 1.12 | No response observed. |
| —CH$_2$CH$_2$CH$_2$CH$_3$ | 2 | H | 5.0 | 5.60 | Stature reduction, early pod set, leaf inhibition, leaf distortion, axillary bud inhibition. |
| | | | 5.0 | 5.60 | Stature reduction, early pod set, enhanced pod set, inhibition of apical development, axillary bud inhibition. |
| | | | 2.5 | 2.80 | Stature reduction, leaf distortion, inhibited pod development. |
| | | | 2.5 | 2.80 | Earlier flowering, enhanced pod set, leaf distortion, axillary bud inhibition, leaf inhibition. |
| | | | 1.0 | 1.12 | Stature reduction, early pod set, leaf distortion. |
| | | | 1.0 | 1.12 | Leaf distortion, axillary bud inhibition, earlier flowering, early pod set. |
| —CH$_2$CH$_2$CH(CH$_3$)$_2$ | 2 | H | 5.0 | 5.60 | Early pod set. |
| | | | 2.5 | 2.80 | No response observed. |

Unexpected plant growth regulating activity was demonstrated which was consistent with previous data obtained from the tests reported in Tables IV and V when the novel N-substituted oxobenzothiazolines of the present invention were further tested according to the procedure described in Example 7.

EXAMPLE 7

A number of soybean plants, variety Williams, are grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 is used as a surfactant.

When the fifth trifoliate leaf (four to five weeks) was fully expanded, the treated plants were compared with the non-treated control plants and the observations recorded.

Table VI below summarizes the results and observations made in accordance with the above procedure.

TABLE VI

| Compound (R) | (n) | (T) | RATE Lbs Acre | RATE Kilos Hectare | Dry Weight[1] % Control | Response |
|---|---|---|---|---|---|---|
| —CH$_3$ | 1 | H | 2.5 | 2.80 | 81 | Leaf alteration, slight leaf burn. |
| | | | 0.5 | 0.56 | 72 | No response observed at application rate. |
| | | | 0.1 | 0.112 | 79 | No response observed at application rate. |
| —CH$_3$ | 2 | H | 2.5 | 2.80 | 67 | Stature reduction, altered canopy, stem distortion, leaf alteration. |
| | | | 0.5 | 0.56 | 93 | Leaf alteration. |
| | | | 0.1 | 0.112 | 77 | Leaf alteration. |
| —C$_2$H$_5$ | 2 | H | 2.5 | 2.80 | 68 | Stature reduction, altered canopy, stem distortion, leaf alteration. |
| | | | 0.5 | 0.56 | 69 | Leaf alteration. |
| | | | 0.1 | 0.112 | 90 | Leaf alteration. |
| —CH(CH$_3$)$_2$ | 2 | H | 2.5 | 2.80 | 70 | Stature reduction, altered canopy, stem distortion, inhibition of apical development, Leaf distortion. |
| | | | 0.5 | 0.56 | 83 | Leaf alteration, altered canopy. |
| | | | 0.1 | 0.112 | 101 | Leaf alteration, altered canopy. |
| —CH$_2$CH$_2$CH$_2$CH$_3$ | 2 | H | 2.5 | 2.80 | 80 | Stature reduction, leaf distortion, altered canopy, inhibition of apical development. |
| | | | 0.5 | 0.56 | 83 | Stature, reduction, leaf distortion, altered canopy, inhibition of apical development. |
| | | | 0.1 | 0.112 | 101 | No response observed at application rate. |

TABLE VI-continued

| Compound (R) | (n) | (T) | RATE Lbs Acre | RATE Kilos Hectare | Dry Weight[1] % Control | Response |
|---|---|---|---|---|---|---|
| —CH₂CH(CH₃)₂ | 2 | H | 2.5 | 2.80 | 84 | Stature reduction, altered canopy, stem distortion, leaf distortion, leaf alteration. |
|  |  |  | 0.5 | 0.56 | 104 | Leaf alteration. |
|  |  |  | 0.1 | 0.112 | 95 | Leaf alteration. |
| —CH₃ | 2 | Cl | 2.5 | 2.80 | 80 | Stature reduction, leaf alteration, altered canopy, slight leaf burn. |
|  |  |  | 0.5 | 0.56 | 75 | No response observed at application rate. |
|  |  |  | 0.1 | 0.112 | 84 | No response observed at application rate. |
| —CH₃ | 2 | OC₂H₅ | 2.5 | 2.80 | 95 | Leaf alteration. |
|  |  |  | 0.5 | 0.56 | 98 | No response observed at application rate. |
|  |  |  | 0.1 | 0.112 | 98 | No response observed at application rate. |

[1]Control = 100%.

The N-substituted oxobenzothiazoline compounds described herein exhibit unexpected properties when used to regulate the growth of desirable crop plants, especially leguminous plants.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

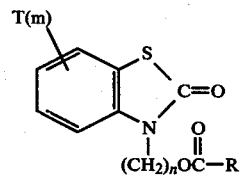

wherein R is alkyl having from 1-5 carbon atoms, T is Chloro, NO₂, alkyl having from 1-5 carbon atoms, or alkoxy having from 1 to 5 carbon atoms, m is 0 or 1, and n is 1 or 2.

2. A compound as defined in claim 1 wherein m is 0.
3. A compound as defined in claim 2 wherein n is 1.
4. A compound as defined in claim 2 wherein n is 2.
5. A compound as defined in claim 1 wherein m is 1.
6. A compound as defined in claim 5 wherein n is 1.
7. A compound as defined in claim 5 wherein n is 2.
8. A compound as defined in claim 1 wherein T is chloro, NO₂, lower alkyl, and lower alkoxy.
9. A method of regulating the natural growth and development of leguminous crop plants which comprises applying to the plant locus an effective plant regulating, non-lethal, amount of a compound of the formula

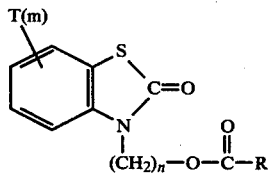

wherein R is alkyl having from 1-5 carbon atoms, T is chloro, NO₂, alkyl having from 1-5 carbon atoms or alkoxy having from 1-5 carbon atoms, m is 0 or 1 and n is 1 or 2.

10. A method as defined in claim 9 wherein said leguminous crop plant is soybean.
11. A method as defined in claim 9 wherein in said plant regulating compound m is 0.
12. A method as defined in claim 11 wherein in said plant regulating compound n is 1.
13. A method as defined in claim 11 wherein in said plant regulating compound n is 2.
14. A method as defined in claim 9 wherein in said plant regulating compound m is 1.
15. A method as defined in claim 14 wherein in said plant regulating compound n is 1.
16. A method as defined in claim 14 wherein in said plant regulating compound n is 2.
17. A method as defined in claim 9 wherein in said plant regulating compound T is chloro, NO₂, lower alkyl and lower alkoxy.
18. A plant growth regulating composition comprising an adjuvant and effective plant growth regulating amount of a compound of the formula

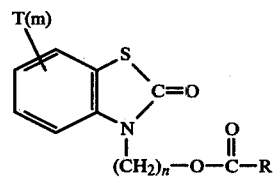

wherein:
R is alkyl having from 1-5 carbon atoms; T is cloro, NO₂, alkyl having from 1-5 carbon atoms, or alkoxy having from 1-5 carbon atoms; m is 0 or 1; and n is 1 or 2.

19. A plant growth regulating composition as defined in claim 18 wherein in said compound m is 0.
20. A plant growth regulating composition as defined in claim 19 wherein said compound n is 1.
21. A plant growth regulating composition as defined in claim 19 wherein in said compound n is 2.
22. A plant growth regulating composition as defined in claim 18 wherein in said compound m is 1.
23. A plant growth regulating composition as defined in claim 22 wherein in said compound n is 1.
24. A plant growth regulating composition as defined in claim 22 wherein in said compound n is 2.

Disclaimer 4,210,439.—*Frederic G. Bollinger*, Creve Coeur, and *John J. D'Amico*, Olivette, Mo. N-SUBSTITUTEDOXOBENZOTHIAZOLINES AND THEIR USE AS PLANT GROWTH REGULATORS. Patent dated July 1, 1980. Disclaimer filed June 23, 1981, by the assignee, *Monsanto Co.*

Hereby enters this disclaimer to claims 1 to 8 of said patent.

[*Official Gazette August 18, 1981.*]